US008227513B2

(12) United States Patent
Suovaniemi et al.

(10) Patent No.: US 8,227,513 B2
(45) Date of Patent: Jul. 24, 2012

(54) FOOD COMPOSITION FOR BINDING ACETALDEHYDE IN MOUTH AND IN DIGESTIVE TRACK, AND METHOD FOR THE PREPARATION OF THE COMPOSITION

(75) Inventors: Osmo Suovaniemi, Helsinki (FI); Mikko Salaspuro, Helsinki (FI); Ville Salaspuro, Espoo (FI); Martti Marvola, Helsinki (FI)

(73) Assignee: Biohit Oyj, Helsinki (FI)

( * ) Notice: Subject to any disclaimer, the term of this patent is extended or adjusted under 35 U.S.C. 154(b) by 0 days.

(21) Appl. No.: 12/622,145

(22) Filed: Nov. 19, 2009

(65) Prior Publication Data

US 2010/0063149 A1    Mar. 11, 2010

Related U.S. Application Data

(62) Division of application No. 11/910,458, filed as application No. PCT/FI2006/000104 on Apr. 3, 2006, now abandoned.

(30) Foreign Application Priority Data

Apr. 1, 2005   (FI) .................................. 20050341

(51) Int. Cl.
*A61K 31/197* (2006.01)
(52) U.S. Cl. ...................................... 514/562
(58) Field of Classification Search .................. None
See application file for complete search history.

(56) References Cited

U.S. PATENT DOCUMENTS

| | | | |
|---|---|---|---|
| 4,472,428 A | 9/1984 | Toru et al. | |
| 4,496,548 A | 1/1985 | Moldowan et al. | |
| 4,528,295 A | 7/1985 | Tabakoff | |
| 4,532,947 A | 8/1985 | Caseley | |
| 5,060,672 A | 10/1991 | Irimi et al. | |
| 5,202,354 A | 4/1993 | Matsuoka et al. | |
| 5,849,330 A | 12/1998 | Marvola et al. | |
| 5,922,346 A | 7/1999 | Hersh | |
| 6,299,867 B1 | 10/2001 | Aoyagi et al. | |
| 2004/0265358 A1 * | 12/2004 | Verhoef et al. | 424/439 |
| 2005/0019427 A1 | 1/2005 | Langeland | |

FOREIGN PATENT DOCUMENTS

| | | |
|---|---|---|
| EP | 0 504 726 A | 9/1992 |
| EP | 1 238 594 A2 | 9/2002 |
| JP | 62-277325 A | 12/1987 |
| JP | 1991-36895 A | 8/1989 |
| JP | 03-074327 | 3/1991 |
| JP | 04 021635 A | 1/1992 |
| JP | 61-16144 A | 4/1994 |
| JP | 2003/055215 A | 2/2003 |
| WO | 9915035 A1 | 4/1999 |
| WO | 99/27941 A | 6/1999 |
| WO | 00/71145 A | 11/2000 |
| WO | 02/36098 A | 5/2002 |
| WO | 02/098405 A1 | 12/2002 |
| WO | 2005/077464 A1 | 2/2005 |

OTHER PUBLICATIONS

Database WPI, Section Ch, Week 198631, Derwent Publications Ltd, London, GB; AN 1986-201667 XP002391658 (Jun. 21, 1986).
Salsapuro et al, *Annals of Medicine*, 28(3):195-200(1996).
Salaspuro et al, *Int. J. of Cancer*, 97:361-364(2002).
Salaspuro et al, *Best Practice and Res. Clin Gastroenterology*, 17(4):679-694(2003).
Salaspuro et al, *Critical Rev. in Clin. Laboratory Sciences* 40(2):183-208 (2003).
Salaspuro et al, *Int. J. of Cancer*, 111:480-483 (2004).
Vakevainen et al, *Aliment Pharmacol Ther.*, 14:1511-1518 (2000).
Vakevainen et al, *Rapid Communication*, 24(6):873 (2000).
Vakevainen et al, *Alcoholism: Clinical and Exp. Res.*, 25(3):421 (2001).
Vakevainen et al, *Scand. J. Gastroententerol*, pp. 649-655 (2002).
Jokelainen et al, *Alcoholism: Clinical and Experimental Research*, 20(7):1210 (1996).
Homann et al, *Carcinogenesis*, 21(4):663-668 (2000).
International Preliminary Report on Patentability, 2006.
WPI/Derwent's Abstract, Accession No. 1991-136895, week 9125, Abstract of JP. 19890211064 (Ajinomoto KK) Aug. 16, 1989.

* cited by examiner

*Primary Examiner* — Brian-Yong S Kwon
*Assistant Examiner* — Jennifer Berrios
(74) *Attorney, Agent, or Firm* — Sughrue Mion, PLLC

(57) ABSTRACT

The object of the invention comprises food compositions, to which one or more acetaldehyde-binding compounds are added. The purpose of the compositions is to reduce the amount of detrimental acetaldehyde in the area of the mouth, the pharynx, the oesophagus, the stomach, and the small and large intestines, and through this, to reduce the risk of developing cancers in these areas.

6 Claims, No Drawings

FOOD COMPOSITION FOR BINDING ACETALDEHYDE IN MOUTH AND IN DIGESTIVE TRACK, AND METHOD FOR THE PREPARATION OF THE COMPOSITION

This is a divisional of application Ser. No. 11/910,458 filed Oct. 1, 2007, which is a National Stage of International Application No. PCT/FI2006/000104, filed on Apr. 3, 2006, claiming priority based on Finland Patent Application No. 20050341, filed Apr. 1, 2005, the contents of all of which are incorporated herein by reference in their entirety.

The invention relates to a food composition wherein at least one acetaldehyde-binding compound has been added thereto and a method for the preparation of such a food composition. The invention also relates to a method for reducing or removing the acetaldehyde contained in a foodstuff from the foodstuff, a composition comprising at least one acetaldehyde-binding compound, and optionally, carries and/or additives suitable for food, which is added to the foodstuff, and the use of acetaldehyde-binding compounds to prepare the food composition.

Both alcohol and smoking are risk factors for upper digestive tract cancers, and the combined use thereof multiplies the risk of developing an upper digestive tract cancer to as much as 150-fold (Salaspuro, M. Best Pract Res Clin. Gastroenterol (2003) 17:679-94 and Francheschi et al. Cancer Res (1990) 50:6502-07).

The first metabolite of alcohol is acetaldehyde. It has been shown to be carcinogenic both to test animals and humans (Salaspuro, M. Crit Rev Clin Lab Sci (2003) 40: 183-208). Alcohol is evenly distributed in the liquid phase of the organs. Hence, after enjoying alcohol and as long as there is alcohol in the organs, the alcohol content in blood, saliva, gastric juice and the contents of the intestine is the same. In that case, the microbes in the digestive tract are capable of oxidizing the alcohol to acetaldehyde. As the aldehyde dehydrogenase enzyme of the liver removes the acetaldehyde thus generated, no alcohol can accumulate in the liver, where the metabolism of alcohol mainly takes place.

Asian heavy drinkers, who have a familial low-activity modification of the aldehyde dehydrogenase-2 (ALDH2) enzyme, have both an increased risk of developing a cancer of the mouth, the pharynx and the digestive tract, and an increased acetaldehyde content of the saliva after consuming alcohol (Väkeväinen et al. (2000) Alcohol Clin Exp Res 24:873-877). Even more common is the ADH3*1 gene/allele (ADH1C at present), which predisposes the heavy drinkers, who have this gene, to the upper digestive tract cancers because of increased local acetaldehyde contents. (Visapää J-P et al. Gut. 2004 June; 53(6):871-6.) In the organism, acetaldehyde is thus formed from alcohol as a consequence of the hepatic metabolism and, locally, in the digestive tract via microbial alcohol dehydrogenase and that of mucous membrane cells (Salaspuro et al, (1996) Ann Med 28:195-200). For example, even after a moderate dose of ethanol (0.5 g/kg), high acetaldehyde contents of a microbial origin (18-143 µM) have been found in human saliva; in other words, acetaldehyde mainly builds up in saliva as an intermediate product of the microbial metabolism; in addition, it is also produced by the mucous membrane cells and salivary glands (Homann et al, Carcinogenesis (1997) 18:1739-1743).

As a consequence of the microbial metabolism, acetaldehyde also builds up in the stomach in the case, where the stomach is free from acid or has been made acid-free by medication (Väkeväinen et al, (2000) Alimentary Pharmacology Ther 14:1511-1518). It has also been shown that acetaldehyde builds up in the large intestine, as its bacteria that represent the normal flora are capable of converting ethanol into acetaldehyde (Jokelainen et al, (1996) Gut 39:100-104).

In the intestines, endogenous ethanol can also be found, i.e. ethanol that is formed in the intestines in oxygen-free conditions under the effect of microbes. Acetaldehyde is formed, when this ethanol comes into contact with oxygen near the mucous membrane, for example.

For atrophic gastritis patients, microbes produce high acetaldehyde contents from ethanol in the stomach, possibly leading to an enhanced gastric cancer risk among atrophic gastritis patients (Väkeväinen et al, Scand J Gastroenterol 2002 (6):648-655).

Acetaldehyde is formed in the mouth, the pharynx and the upper respiratory ducts also as a consequence of smoking and exposure to air contamination (passive smoking, fumes, exhaust gases, etc.). It has been proven that chronic smoking increases the acetaldehyde production of a microbial origin in saliva. Salaspuro et al. (2004) Int J Cancer, 2004 Sep. 10; 111(4):480-3) have proven that the average in vivo acetaldehyde concentration in saliva is about two times higher for smokers than for non-smokers after enjoying ethanol, the control time being 160 minutes. During the time consumed by smoking, the in vivo acetaldehyde in saliva was increased to ten-fold from the level it was after enjoying ethanol only. During active smoking, the acetaldehyde in saliva was increased to a value of 261.4±45.5 µM from the basic level. The average amount of saliva secreted by a human is 1.5 litres per day. The areas of influence of the acetaldehyde contained in the saliva include the mouth, the pharynx, the aesophagus and the ventricle.

Pharmaceutical compositions containing compounds that bind acetaldehyde are known from before, their effect being based on the reaction of the effective substances with the acetaldehyde inside blood and/or cells, for example, U.S. Pat. No. 5,202,354, U.S. Pat. No. 4,496,548, U.S. Pat. No. 4,528, 295, U.S. Pat. No. 5,922,346.

Acetaldehyde, which is formed in the organism when alcohol is consumed and thereafter, also causes physiological symptoms called a hangover. Previously, efforts have been made to decrease the symptoms caused by acetaldehyde by taking preparations containing ascorbic acid, thiamine, cysteine or cysteic acid, and flavonoids or flavonoid complexes in a form of orally taken tablets in connection with, before or after consuming alcohol. When swallowed, the effective substances go to the stomach and from there into the blood circulation (Matsuoka, U.S. Pat. No. 5,202,354 and Moldowan et al, U.S. Pat. No. 4,496,548).

Suggestions have been made so as to use preparations containing amino acids, such as L-cysteine, methionine, taurine or arginine, ascorbic acid, vitamins A and E, which are sucked or chewed in the mouth, to reduce the effect of detrimental free radical compounds, which are formed when using tobacco products or being exposed to the same. It is believed that, after being absorbed, amino acids affect various tissues (Hersch, U.S. Pat. No. 5,922,346, Hersch, International Patent Application No PCT/US98/12617).

Publication WO 02/36098 suggests the use of compounds containing a free sulphhydryl and/or amino group for a local and long-term binding of acetaldehyde from saliva, the stomach or the large intestine. The compounds were mixed with a substance that enabled them to be released for at least 30 minutes in the conditions of the mouth, the stomach or the large intestine.

As on the basis of recent studies, acetaldehyde plays a considerable part in the pathogenesis of the upper digestive tract cancers, there is a need to find alternative ways to bind acetaldehyde in the mouth and the digestive tract in a harmless manner.

The purpose of the present invention is to provide new compositions, which are suitable to be used in foodstuffs and which can be consumed to reduce the acetaldehyde content in the entire digestive tract, and especially in the mouth, the pharynx, the oesophagus, the ventricle, and the large intestine, or to remove the acetaldehyde.

In principle, the acetaldehyde can originate in any source, such as a foodstuff containing acetaldehyde. The acetaldehyde can have been formed from the ethanol contained in the foodstuff or it can have been formed from endogenous ethanol occurring in the organism or from the precursors of the acetaldehyde as a consequence of the metabolism, for example, sugars—acetate—acetaldehyde. The purpose of the invention is to reduce the risk of developing cancers of the mouth, the pharynx, and the digestive tract, which are caused by the acetaldehyde occurring in the said areas.

The present invention is directed at a food composition, to which one or more acetaldehyde-binding compounds have been added.

To be more precise, the composition according to the invention is characterized in that, which is presented in the characterizing part of Claim 1.

According to the invention, compounds containing one or more free sulphhydryl and/or amino groups are added to foodstuffs, which are consumed with the object of reducing the risk of developing cancers of the mouth, the pharynx, the digestive tract, especially the ventricle and the large intestine. Consuming the food compositions according to the invention mainly binds acetaldehyde locally, but it may also have a systemic effect.

Another object of the invention comprises the method wherein the acetaldehyde-binding compound is added to a selected foodstuff for the preparation of the food composition.

The dosing of pharmaceutical compositions containing acetaldehyde-binding compounds, for example, in aqueous solutions is presented by patent publication U.S. Pat. No. 4,528,295. Patent publication WO 02/098405 suggests the use of cysteine-containing inhibitors to inhibit liver fibrosis and liver diseases, such as cirrhosis. According to the publication, the inhibitor can be in the form of drugs or foods or drinks. Publications JP 4021635 and JP 61134313 suggest adding a dipeptide that contains alanine or a substance that contains alpha-alanine to drinks to reduce the toxicity of the acetaldehyde. However, the known technique does not suggest the addition of compounds capable of binding acetaldehyde to foodstuffs, especially to the food products directed at consumers.

The present invention also relates to food compositions, which contain acetaldehyde or where acetaldehyde has formed, and to which one or more acetaldehyde-binding compounds have been added. According to the invention, the acetaldehyde-binding compounds can be allowed to fully or partially bind the acetaldehyde in the foodstuff. If the acetaldehyde-binding compound has been added to the foodstuff in an amount sufficient to bind the acetaldehyde in the food composition, the foodstuff delivered to the consumers does not contain essential amounts of acetaldehyde, but only its harmless degradation products.

Accordingly, the object of the invention comprises a method to reduce or remove the acetaldehyde contained in a foodstuff comprising the steps of
  measuring the acetaldehyde contained in the foodstuff;
  adding to the foodstuff at least such an amount of acetaldehyde-binding compound that it is capable of binding the acetaldehyde in the foodstuff; and
  allowing the acetaldehyde-binding compound to react with the acetaldehyde in the foodstuff in suitable conditions for long enough, so that from the bound acetaldehyde is formed compounds harmless in the organism.

Another object of the invention comprises a solid or liquid composition which comprises at least one acetaldehyde-binding compound and optionally, carries and/or additives suitable for food that is added to the foodstuff.

A further object of the invention comprises the use of the acetaldehyde-binding compound to prepare the food composition, characterized in that the acetaldehyde-binding compound is added to the foodstuff in an amount that binds the acetaldehyde, which is naturally formed or which goes to the mouth, the pharynx, or the digestive tract in connection with consuming alcohol and/or smoking, or which forms therein.

The invention provides considerable advantages. The food compositions containing acetaldehyde-binding compounds can be used to reduce the risk of developing the cancer of the mouth, the pharynx, the oesophagus, the ventricle, and the small and large intestines. In particular, the compositions according to the invention can be used for large-scale consumers of alcohol, smokers and those, who have a familial low-activity modification of the aldehyde dehydrogenase-2 (ALDH2) enzyme or the ADH3*1 gene/allele (ADH1C*1 at present), and for those who suffer from atrophic gastritis. The use of the compositions according to the invention is also of benefit to those who consume moderate amounts of alcohol or who consume foodstuffs that contain small contents of alcohol or acetaldehyde. By adding the compounds to the food products aimed at consumers, the use of acetaldehyde-binding compounds can be extended and made a part of everyday life; on the other hand, it can yet be directed at groups of people who use alcohol on a regular basis or who smoke or have the familial low-activity modification of the aldehyde dehydrogenase-2 (ALDH2) enzyme or the ADH3*1 gene/allele (ADH1C at present).

Removing or reducing the acetaldehyde, which is in foodstuffs or which forms in the foodstuffs, before the foodstuff is delivered to the consumers, reduces or removes the amount of acetaldehyde entering the mouth or the digestive tract and reduces the risk of contracting cancers of these areas. If the acetaldehyde-binding compound, which is added to bind the acetaldehyde in the foodstuff, is fully consumed to bind the acetaldehyde, there is the advantage that the acetaldehyde-binding compound will not give the food composition an extra flavour. On the other hand, if the acetaldehyde-binding compound is not consumed to bind the acetaldehyde in the foodstuff, the acetaldehyde-binding compound travels along with food to the mouth and the digestive tract to bind the acetaldehyde in these areas.

In the following, the present invention is examined more closely with the aid of a detailed description and examples of application.

A "food composition" refers to any solid, semi-solid, or liquid foodstuff, also a drinkable liquid, which is suitable for food.

A "food product" refers to any foodstuff that is suitable for food, especially one that is packed, bottled or, in another way, prepared to be delivered to consumers. The product meant for consumers also means, among others, that the markings of the product be intelligible to consumers. The food product can also be, for example, a food product that is delivered to a restaurant or a shop to be conveyed to the consumers.

A "drink composition" refers to any drinkable liquid that is suitable for food.

A "drink product" refers to any drinkable liquid, especially one that is packed or bottled to be delivered to consumers. Thus, the product does not refer to drinking water or juice supplied to humans or animals in laboratory tests, for example.

"Domestic water" refers to water that is delivered from the water utility to the consumers; it can also be called tap water.

A "product that is added to the foodstuff" refers to a food composition in particular, which is packed, bottled or, in some other way, prepared for consumers; for example, provided with clear markings for the consumer.

A "consumer package" refers to a foodstuff package aimed at consumers, such as a food or drink package, which is packed or bottled or, in some other way, prepared for the consumer. The package preferably contains clear markings indicating the contents, the purpose of use and the way of using the product. The markings for consumers, for example, mean that no pharmaceutical education should be needed for one to be able to read the markings.

The term "consumer" herein is used in its conventional sense. Furthermore, the consumer may refer to the employees of a shop selling foodstuffs, a restaurant or the food industry.

The digestive tract herein refers to the human or animal digestive tracts, the human digestive tract, in particular. The methods described by the invention could also be used to reduce the cancers of animal digestive tracts.

An "acetaldehyde-binding substance" refers to a compound containing one or more free sulphhydryl and/or amino groups, preferably a sulphhydryl and an amino group. "Compound" may be used to refer to one or more compounds.

Cysteine and its derivatives are especially well suited to the purpose according to the invention. The most suitable amino acids for the use according to the invention comprise L- and D-cysteines, acetylcysteine or the derivatives of cysteine, or salts, especially water-soluble derivatives or water-soluble salts, which function in the same way as the L- or D-cysteines. The most preferred compound is L-cysteine.

The "binding of acetaldehyde" refers to a chemical reaction between the acetaldehyde and the compound that has a free sulphhydryl and/or amino group, wherein the acetaldehyde jointly with the "acetaldehyde-binding substance" forms a larger molecule and water can be formed in the reaction. For example, when reacting with cysteine, the acetaldehyde binds itself both to the sulphhydryl and the amino group and forms 2-methyl-L-thiazolidine-4-carboxylic acid and water. The acetaldehyde can bind itself to the amino group of almost any protein, whereby Schiff's base or a 2-methyl-imidazole ring is formed.

According to the invention, the compounds obtained from acetaldehyde by chemically binding are safe for the organism.

Suitable compounds for binding acetaldehyde in the organism also include the compounds according to the formula (I):

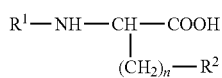

(I)

wherein
$R^1$ is hydrogen or an acyl group with 1-4 carbon atoms;
$R^2$ is a sulphhydryl or sulphone group;
n is 1 or 2.

The scope of the invention also includes salts of the compounds according to Formula I, water-soluble salts in particular.

Amino acids or other compounds that suitably bind acetaldehyde and contain a free sulphhydryl (SH) and/or amino ($NH_2$) group include, for example:

L-cysteine,
D-cysteine,
cysteic acid,
cysteine glycine,
threo or erythro-β-phenyl-DL-cysteine,
β-tetramethylene-DL-cysteine,
methionine,
D-penicillamine and its dipeptides with N-terminals,
semicarbazide,
reduced glutathione,
β-mercaptoethylamine,
D, L-homocysteine,
N-acetylcysteine,
L-cysteinyl-L-valine,
β-β-tetramethylene-DL-cysteine,
cysteinyl-glycine,
mercaptoethylglycine,
tre-(5)-β-phenyl-DL-cysteine,
erythro-beta-phenyl-DL-cysteine,
cysteine hydrochloride,
thiaminhydrochloride,
sodiummetabisulphite,
mercaptanes.

The scope of the invention also includes salts of the compounds, water-soluble salts in particular.

However, only those acetaldehyde-binding compounds, which are suitable for foodstuffs, can be applied to the products according to the present invention. These compounds should not cause a health hazard in the amounts used.

A "harmful/carcinogenic content of acetaldehyde" in the human mouth, oesophagus, ventricle, and large intestine is 20 to 800 μmol/l of saliva or the contents of the intestine, a content of as low as about 20 to 50 μM causing carcinogenic mutations on the cell level. Hence, it would be advisable to aim at a zero concentration of acetaldehyde in these areas.

Keeping the acetaldehyde content essentially lower than without the use of the food composition means that the acetaldehyde content should be kept at a level that is at least 20%, preferably over 40%, and most preferably over 60% lower than when not using the composition according to the description of the invention.

Such a harmful or carcinogenic content of acetaldehyde in the human mouth, oesophagus, stomach or large intestine can be obtained in connection with consuming alcoholic drinks, particularly strong alcoholic drinks, or foodstuffs containing alcohol, as a consequence of smoking or when consuming products containing acetaldehyde.

"Alcoholic drinks" are ethanol-containing drinks, their ethanol content varying within 0.7% by volume and 84% by volume."

"Alcoholic foodstuffs" refer to foodstuffs containing at least 0.7% of ethanol. Such foodstuffs can be, for example, fermented juices or preserves, or foodstuffs preserved with small amounts of alcohol, pastries, jellies, and mousse seasoned with liqueur or corresponding products containing alcohol.

The use of the products according to the invention can be of benefit even, when light alcoholic drinks are enjoyed or foodstuffs are consumed, which contain small amounts of alcohol.

Some foodstuffs as such can also contain acetaldehyde. Acetaldehyde is contained in foodstuffs, which have ethanol that is generated in connection with fermentation, such as beer, cider, wine, home-brewed beer, and other alcoholic drinks, as well as many juices. In certain foodstuffs, such as some milk products, acetaldehyde is used for preservation purposes and to add flavour, or the acetaldehyde is formed in the product as a consequence of microbial activity. For example, sugary juices or sugar-containing foodstuffs, in general, provide a good substrate for microbes. High concentrations of acetaldehyde are formed, for example, in fermented milk products, such as yoghurt. The microbes used to make yoghurt produce acetaldehyde in the yoghurt. As for alcoholic drinks, sherry and Calvados contain especially large amounts of acetaldehyde.

The amount of acetaldehyde in a foodstuff can be defined by standard methods that are well known by those skilled in the art, such as liquid or gas chromatographic methods. Acetaldehyde can be defined, for example, by means of the gas chromatographic method, which is described in the publication Homann et al. 1997. High acetaldehyde levels in saliva after ethanol consumption: Methodological aspects and pathogenic implications. Carcinogenesis 18:1739-1743, (see also Salaspuro V and Salaspuro M: Synergistic effect of alcohol drinking and smoking on in vivo acetaldehyde concentration in saliva. Int J Cancer 2004; 111:480-483). In that case, it is possible to calculate the amount of acetaldehyde-binding compound that is needed to bind the acetaldehyde in the foodstuff. If the acetaldehyde concentrations in the foodstuff are from 50 to 500 µM, for example, the amount of acetaldehyde-binding compound, such as cysteine, to bind the same, is about 0.1 to 5.0 mM according to our studies; in some cases, a cysteine concentration of 1 to 10 mM may be enough; in other words, the amount of cysteine to be added is about 12.1 mg/l to 6.05 g/l or, correspondingly, from 121 mg/l to 1.21 g/l of foodstuff. Naturally, the amount of acetaldehyde-binding compound that is added to the foodstuff can be higher, if the idea is to carry the acetaldehyde-binding compound to the organism along with the foodstuff.

The compounds capable of binding acetaldehyde should be allowed to react with the acetaldehyde in the food composition for a sufficiently long time in suitable conditions. It is preferable to mix the acetaldehyde-binding compounds with the product as well as possible. The reaction is preferably allowed to take place at room temperature during 5 to 30 min, preferably during 5 to 15 min.

"In connection with consuming alcoholic drinks" herein refers to the period of time that begins from starting to enjoy alcohol and ends, when there is no more alcohol in the blood.

"In connection with smoking" herein refers to the period of time that begins from starting to smoke and ends, when smoking is stopped.

The foodstuff, to which one or more acetaldehyde-binding compounds are added, can comprise cereal or baking products, milk, milk products or, generally, milk dishes, meat, meat products or meat dishes, fish, fish products or fish dishes, fat, oil, fat or oil products, eggs, potatoes, confectionery, fruit or berry dishes, vegetables, vegetable dishes, salads, salt, sugar, sweets, spices, relishes and various dietary supplements, snacks, and various drinks and alcoholic drinks, health foods and preserved foods. On the whole, the acetaldehyde-binding compound(s) can be added to any foodstuff aimed at consumers. Typically, the foodstuff is packed in larger or smaller quantities and it is delivered directly to the consumer or, for example to a restaurant or a shop, which sells the foodstuff in smaller quantities to the consumers.

In particular, it is preferable to add acetaldehyde-binding compounds to foodstuffs that remain in the stomach for a longer period of time, typically, more than half an hour or to foodstuffs or substances used in foodstuffs, which do not decompose or which decompose poorly in the digestive tract and thus work as carriers of the acetaldehyde-binding compounds, carrying them deeper into the intestines.

According to a preferred embodiment of the invention, the acetaldehyde-binding compound(s) is added to various cereal or bakery products, such as buns to serve with coffee, biscuits, crackers, bread, breakfast cereals, sugary pastries, salty pastries, flour, pasta, pizza, porridge, or rice and various rice products, corn and corn products.

It is preferable to add the acetaldehyde-binding compound to various preserves or their preserving liquid, e.g., preserved vegetables or greens, such as pickled cucumbers, pickles, preserved sweet peppers, tomatoes, squash or mushrooms.

According to another preferred embodiment of the invention, the acetaldehyde-binding compound(s) is added to milk or milk products, such as milk desserts, milk sauces, sour milk, soured whole milk, cheese, ice-cream or yoghurt. In particular, it is preferable to add the acetaldehyde-binding compounds to products that remain in the stomach for a longer period of time, such as sour milk, soured whole milk, and yoghurt.

According to another preferred embodiment of the invention, the acetaldehyde-binding compound(s) is added to various snacks, such as potato chips, corn chips, cheese snacks, popcorn, nuts, raisins, almonds, crackers, and dried fruits.

As high acetaldehyde contents occur both in the mouth and the digestive system in connection with enjoying alcohol and smoking, in particular, it is preferable to add acetaldehyde-binding compound(s) to products, which are possibly consumed in connection with drinking alcohol or smoking, in particular. Such products include various snacks and savouries. On the other hand, acetaldehyde-binding compound(s) can be added to food that is served in connection with enjoying alcoholic drinks, for example. This can be effected by adding a seasoning mixture containing acetaldehyde-binding compounds to meat or fish dishes. As seasoning mixtures as such have a strong taste, the taste of the acetaldehyde-binding compounds is hidden under the taste of the mixture.

The amount of acetaldehyde-binding compound(s) that is added depends on the amounts of these foodstuffs the consumer is most likely to enjoy at one time. The amount of added substances also depends on, whether the foodstuff in question already contains acetaldehyde-binding compounds, such as cysteine. The amount of substances to be added also depends on, whether the foodstuff already contains acetaldehyde. For example, 1 to 5000 mg/kg, preferably 5 to 4000 mg/kg, more preferably 5 to 3000 mg/kg, even more preferably 5 to 2000 mg/kg, still more preferably 5 to 1000 mg/kg, even more preferably 5 to 500 mg/kg, even more preferably 5 to 300 mg/kg, most preferably 5 to 100 mg of acetaldehyde-binding compound per kilo of food composition can be added to the product. The amount added to salted peanuts or a steak, for example, can be 1 to 500 mg, typically 5 to 500 mg of cysteine/100 g. The amount of added acetaldehyde-binding compounds also depends on how well the foodstuff in question is able to cover the taste of the acetaldehyde-binding compounds. When calculating the amount of a suitable acetaldehyde-binding compound per day, it is preferably no more than 100 mg per a kilo of a person's weight, more preferably no more than 80 mg/kg, even more preferably no more than 60 mg/kg, still more preferably no more than 40 mg/kg, further and more preferably no more than 20 mg/kg.

The amount of acetaldehyde-binding compound is most preferably no more than 10 mg/kg, preferably no more than 5 mg per a kilo of a person's weight. A single dose of acetaldehyde-binding compounds is preferably no more than 5000 mg, preferably no more than 4000 mg, more preferably no more than 3000 mg, even more preferably no more than 2000 mg, still more preferably no more than 1000 mg, more preferably no more than 500 mg, even more preferably no more than 400 mg, most preferably no more than 300 mg, suitably 100 to 300 mg, typically 100 to 200 mg.

According to a preferred embodiment of the invention, the acetaldehyde-binding compound(s) is added to various drinks, such as juices, sports drinks, soft drinks, spring water, waters, coffee and tea, milk, sour milk, special drinks, such as soy drink.

It is preferable to add acetaldehyde-binding compounds, for example, to mineral waters, soda waters or waters that are served together with alcoholic drinks, or to dilute the same. In that case, the drink may have a slight taste, such as the taste of lemon, which slightly covers the possible taste of the acetaldehyde-binding compounds.

It is especially preferable to add the acetaldehyde-binding compound(s) to various alcoholic drinks, beer, wine and strong alcohol. Regarding these, it is preferable to add the acetaldehyde-binding compound particularly to drinks that as such have high acetaldehyde contents. It is especially preferable to add acetaldehyde-binding compounds to ice cubes, for example, as the acetaldehyde-binding compounds contained in them dissolve at a suitable pace during the time the alcohol or other drinks are being consumed.

According to a preferred embodiment of the invention, the acetaldehyde-binding compound(s) is added to domestic water. The compounds can be added already at the water utility at a suitable process stage before the water is delivered to the consumers. Alternatively, consumers may have at their disposal a special tap having a device connected thereto distributing acetaldehyde-binding compounds, such as an adapter or a filter attached to the end of the tap, from which for example cysteine is dissolved in the tap water. An alternative structure may be a distributing device, such as an automat, which mixes acetaldehyde-binding compounds with the desired drinks, such as soft drinks, beer or mineral water. It is preferable, if such a distributor can be switched on and off, when so desired. Such a distributor or tap adapter is also advantageous in restaurants, where water, ice or other drinks containing acetaldehyde-binding compounds could be served to the customers in connection with selling and serving alcoholic drinks and tobacco. Such a distributor or tap adapter is also advantageous in hospitals that treat patients, who suffer from atrophic gastritis or use preventive medication for gastric acid secretion, or other patients who have exceptional problems with acetaldehyde.

The adapter that is connected to the tap has preferably a structure that allows the adapter to be attached to the tap so that the water coming from the tap runs through the adapter. A carrier, such a filter, which releases one or more acetaldehyde-binding compounds, can preferably be connected to the adapter, water running through the filter, whereby the acetaldehyde-binding compound dissolves in the water coming from the tap along with a water jet. The adapter can preferably be switched off, when so desired.

The adapter according to the description can also be used in treating liquids other than water. For example, beer, soft drinks and mineral water can be dosed through such an adapter.

Acetaldehyde-binding compounds can be added to mineral waters, spring waters or other bottled or packed waters in connection with the bottling/packaging.

Alternatively, a product, which is intended to be added to a certain amount of liquid or solid or semi-solid foodstuff, can be distributed to consumers. Depending on the amount of certain foodstuffs usually consumed, the amount of acetaldehyde-binding compounds in the product added to the foodstuff can be calculated accurately enough and give dosing instructions to the consumers. The product can be, for example, suited to a bottled consumer package, whereby it will be no problem for the consumer to calculate the adequate quantity of dosing.

The acetaldehyde-binding compound is added to drinkable liquids, for example, in an amount of 1 to 5000 mg/l, preferably 5 to 4000 mg/l, more preferably 5 to 3000 mg/l, even more preferably 5 to 2000 mg/l, still more preferably 5 to 1000 mg/l, more preferably 5 to 500 mg/l, more preferably 5 to 300 mg/l, most preferably 5 to 100 mg of acetaldehyde-binding compound per liter of drink product. For example, 5 to 2000 mg/l of cysteine can be added to mineral water, and 50 to 500 mg to 8 cl of cognac.

When preparing the food compositions according to the description of the invention, the acetaldehyde-binding compounds can be added in a solid or liquid form as such or with various carriers or additives. Several acetaldehyde-binding compounds, such as cysteine, can be added as aqueous solutions to foodstuffs, or aqueous solutions can be made from the compounds. As the acetaldehyde-binding compound in a soluble form is capable of immediately binding acetaldehyde in the stomach, when going to the stomach, drinks containing acetaldehyde, cysteine in particular, work effectively. In addition to the solid form and the solution, the acetaldehyde-binding compounds can also be added to foodstuffs as various mixtures, dispersions, gels or emulsion, for example. It is preferable to add the acetaldehyde-binding compound in a form, such as gel, which releases the acetaldehyde-binding compound in a prolonged way. Such gels and other products are described in publication WO 02/36098. The acetaldehyde-binding compound can also be added with oil or as a mixture of water and oil.

The invention also relates to a solid, semi-solid or liquid product that is added to foodstuffs, containing at least one acetaldehyde-binding compound. Such a product can contain liquid or solid carriers or additives suitable for foodstuffs. The dosage of the product is preferably given per a certain foodstuff portion. The dosages and markings given to the consumers should be easy to read and understand. Suitable carriers and auxiliary substances include, for example, various powdery or granular substances, carbohydrates, starch, fibres, cellulose, proteins, glycoproteins, sugar alcohols, sugars, salt, spices, and spice mixtures, products dosed in liquid form, such as various aqueous solutions, oils, syrup and other carriers and auxiliary substances suitable for foodstuffs. The product can also contain various fillers, flavoring agents, scents, stabilizers, buffers and/or preservatives.

According to a preferred embodiment of the invention, the acetaldehyde-binding compound can be added to a food, nutritional and/or drink component, which is capable of conveying the acetaldehyde-binding compound all the way to the small intestine and especially to the large intestine. Such components may comprise various substances, which do not decompose or which decompose poorly in the digestive tract, such as cellulose, the derivatives of cellulose, glycoproteins, such as lactulose, or substances working in a corresponding way.

According to another preferred embodiment of the invention, the food composition can contain acetaldehyde-binding compounds in a protected form so that the compounds are not released until in the small intestine, at the end of the small intestine, in particular, and in the large intestine, especially at its beginning. The protection of the acetaldehyde-binding compound can be provided, for example, by preparing pharmaceutical preparations, such as granules, pellets, etc., which contain the acetaldehyde-binding compound and which are coated with a polymer film that is not dissolved until the pH in its environment is 6.5 or higher. Alternatively, the protection can be provided, for example, by means of a component that does not dissolve until under the effect of the enzymes secreted by the bacteria in the large intestine. The component can be, for example, a polymer, which can be used as a filling agent in the preparation or in the granules contained by the preparation (WO 02/36098).

A film coating made of polymers, which does not dissolve in the acidic environment of the stomach, can be formed on pharmaceutical tablets, capsules or granules, (e.g., D.R. Friend, Oral Colon-Specific Drug Delivery, CRC Press, Florida, ISBN 0-8493-6688-7, 1992). Enteric polymer refers to a polymer, the solubility of which depends on the pH. The solution pH of the film-forming polymer is preferably 6.0 to 7.5, most preferably 6.5 to 7.0.

According to the description of the present invention, the acetaldehyde-binding compound(s) is preferably placed in the foodstuff inside pharmaceutical preparation, such as granules of pellets that are coated with an enteric film. When the granules reach the end of the small intestine or the large intestine, the film is dissolved and the acetaldehyde-binding compounds are released and they act on the area of release.

The polymer film can be formed, for example, from cellulose acetatephtalate, (CAP), such as the quality sold under Aquateric™, a methacrylic acid derivative, such as Eudragit-S™, hydroxypropyl methylcellulose phthalate, or hydroxypropyl methycellulose acetate succinate or the like, such as the grades sold under the trade name Aqoauat™. The granules and pellets coated with the enteric film and the preparation thereof are described in patent publication WO 02/36098.

An enteric tablet, the film coating of which does not dissolve until at the end of the small intestine or at the beginning of the large intestine, can have the following structure, for example. The amount of enteric polymer that forms the film can be 5 to 20%, most preferably 10 to 15% of the whole mass of the tablet. The filler can comprise pharmaceutical additives that do not swell, such as calcium hydrogen phosphate.

The preparation can also comprise granules that contain an acetaldehyde-binding substance and are coated with an enteric film. The amount of film-forming enteric polymer in the entire mass of the granule can be 5 to 30%, most preferably 15 to 25%. The granule can comprise 20 to 40%, preferably about 30% of filler poorly soluble in water, such as calcium hydrogen phosphate.

The binder of the granule that is coated with the enteric film can be an enteric polymer, the solution pH of which is 6.0 to 7.5, most preferably 6.5 to 7.0. The amount of binder in the granule is 2 to 5%, preferably 3 to 4%.

The preparation according to the invention can also be a tablet containing the enteric coated granules described above, on which an enteric film has also been made. The tablet made for such a preparation not only comprises enteric granules, but also a filler suitable for direct compression, such as microcrystalline cellulose, the amount of which in the tablet can be 30 to 70%, preferably 40 to 60%.

The foodstuff can be any suitable solid, semi-solid or liquid foodstuff. It can preferably be a foodstuff with a pH of below 7, such as sour milk products, e.g., yoghurt, sour milk or sour whole milk.

In addition to the pH suitable for the purpose according to the invention, one advantage of the sour milk products is also the fact that the duration of the product is fairly short, whereby a premature release of the acetaldehyde-binding compounds is unlikely. By nature, there is ethanol in the human large intestine; therefore, it is justifiable to add acetaldehyde-binding compounds to products, which are consumed quite widely. A considerable advantage is that the taste of the acetaldehyde-binding compounds is not an issue, as the release of the compounds will not occur until in the small and large intestines. In that case, the compounds can be added in large quantities, when so desired, i.e., even in amounts, which at their highest can safely be recommended to humans per a kilo of weight.

Tablets, capsules or granules, which remain in the stomach for a long time, can also be added to the food composition. The tablets, granules or corresponding preparations can be prepared so that they adhere to the mucous membrane of the stomach or float in the contents of the stomach. The preparations can be rendered fixable to the mucous membrane of the stomach by using as additives cationic polymers, such as various chitosan grades. Preparations that float in the stomach are provided by using polymers (e.g., alginic acid) that form a gel and by adding to the preparation sodium hydrogen carbonate, as described in patent publication WO 02/36098.

The preparation that locally binds acetaldehyde in the stomach can be a tablet that forms a gel in the stomach or a capsule comprising a mixture of powder or granules that forms a gel. In addition to the acetaldehyde-binding substances, the preparation comprises polymers that form a gel in the stomach, such as chitosans, alginates, sodium carboxymethylcellulose grades, carbomers or aluminium hydroxide. To advance floating in the stomach, the preparation can also comprise sodium hydrogen carbonate.

The amount of polymers in the preparation is 10-50%, preferably 15-40%, and most preferably 20-30%.

The amount of sodium hydrogen carbonate can be 10-30%, preferably 20% of the amount of polymers.

The preparation, which is added to the food composition and which binds acetaldehyde in the stomach, can be a tablet or granule preparation, wherein the acetaldehyde-binding substance is mixed with the fillers needed, and granulated thereafter by using enteric polymers as binders. The binder used can be any known enteric polymer, most preferably a polymer with a solution pH of 6 to 7, and most preferably the polymer is any of the methacrylate derivatives, which are known by the trade names Eudragit L and Eudragit S. The amount of enteric polymer in the preparation is preferably 2 to 5%, most preferably 3 to 4%.

The preparation that locally binds acetaldehyde in the stomach can be a liquid preparation, i.e., a mixture comprising, in addition to the acetaldehyde-binding substance, also sodium alginate, aluminium hydroxide, sodium hydrogen carbonate, and water. The amount of water in the whole preparation can be 70 to 90%, most preferably about 75 to 85%. The amount of sodium alginate in the preparation is preferably 2 to 10%, most preferably about 5%, and the amount of aluminium hydroxide is preferably 5 to 15%, most preferably about 10%.

The relative composition of the preparation comprising granules can be as follows, for example:

| Acetaldehyde-binding substances | 60 parts |
|---|---|
| Chitosan | 10 to 40 parts |
| Calcium hydrogen phosphate | 0 to 30 parts |

The relative composition of the liquid preparation can be as follows, for example:

| Acetaldehyde-binding substances | 10 parts |
|---|---|
| Sodium alginate | 2-10 parts |
| Aluminium hydroxide | 5-15 parts |
| Sodium hydrogen carbonate | 1-2 parts |
| Water | 70-80 parts |

The dosage unit, which is consumed with the foodstuff and which goes to the intestines, can preferably be 50 to 500 mg of acetaldehyde-binding substance, preferably 50 to 300 mg, and most preferably 100 to 200 mg.

Other preparations, which are described in patent publication WO 02/36098 and which release compounds that are able to bind acetaldehyde in the stomach in a prolonged way, or preparations, which release compounds that are able to bind acetaldehyde in the small or the large intestines, can also be added to the food composition.

It is of advantage to add preparations that release compounds that are able to bind acetaldehyde to foodstuffs as compositions or products that are aimed for adding to the foodstuffs. In that case the acetaldehyde-binding substances are not released too early, just in connection of consuming the foodstuff or in the intestine.

Advantages similar to those that are obtained when adding to the foodstuff preparations, which are not released until in the small or large intestines, are obtained when acetaldehyde-binding substances are added to the foodstuff as preparations, which release compounds that bind acetaldehyde in the stomach in a prolonged way.

The above-mentioned preparations, which release compounds that bind acetaldehyde in the stomach, or which release compounds that bind acetaldehyde in the small/large intestine, can also be added to the foodstuff simultaneously. In addition, the acetaldehyde-binding compounds can be added to the foodstuff in a form that binds the acetaldehyde contained in the product even before consuming the product.

EXAMPLE 1

In the test, the capability of cysteine to bind acetaldehyde from light alcohol drinks and milk products, such as yoghurt, was examined.

The amounts of acetaldehyde in four Finnish yoghurts and three beers were measured by means of a standardized method (Homann et al. 1997. High acetaldehyde levels in saliva after ethanol consumption: Methodological aspects and pathogenic implications. Carcinogenesis 18:1739-1743).

The average acetaldehyde concentration (±SEM) in the beers was 146±30 µM. L-cysteine was added to the beers so that the final cysteine concentration of the product was 0 (the control), 0.1, 3 and 10 mM (i.e., 0 mg/l, 12.1 mg/l, 363 mg/l and 1210 mg/l); thereafter, the beers were incubated for 5 min at room temperature. Thereafter, the acetaldehyde contents were measured by means of a gas chromatograph. The acetaldehyde concentrations after the treatment were 146±30 µM, 133±32 µM, 26±9 µM and 10±3 µM, correspondingly.

In the yoghurt, the acetaldehyde concentrations were 419±53 µM, on an average. L-cysteine was added so that the cysteine concentrations in the final product were 0 (the control), 0.1, 3 and 10 mM (i.e., 0 mg/l, 12.1 mg/l, 363 mg/l, and 1210 mg/l); thereafter, the yoghurts were incubated for 5 min at room temperature. The acetaldehyde concentrations after the treatment were 419±53 µM, 240±42 µM, 55±15 µM, and 15±2 µM.

It was possible to eliminate as much as 3 mM of cysteine (363 mg/l) from over 80% of the acetaldehyde in the products.

EXAMPLE 2

10 mM of L-cysteine is added to various products, such as lemon-flavoured mineral water, milk, sour milk, and yoghurt. As part of the cysteine is consumed in binding the acetaldehyde in the product, the amount of cysteine coming into the system in products, which contain acetaldehyde, is about 7 mM, i.e. about 848 mg/l. The amount of cysteine coming into the system in a product not containing acetaldehyde is about 1210 mg/l.

EXAMPLE 3

Granules coated with an enteric film are prepared, containing L-cysteine, as described in patent publication WO 02/36098. The solution pH of the film is about 7.

| Enteric granules | L-cysteine | 100 mg |
|---|---|---|
| | calcium hydrogen phosphate | 30 to 50 mg |
| | enteric polymer | 40 to 60 mg |

The granules are added to the yoghurt in an amount such that the amount of L-cysteine is 1000 mg/l of yoghurt, whereby the amount of L-cysteine obtained from 2 dl of yoghurt should be 200 mg of L-cysteine, conveyed all the way to the end of the small intestine or the beginning of the large intestine.

Correspondingly, preparations can be made for the stomach, as described in patent publication WO 02/36098.

EXAMPLE 4

The granules releasing cysteine in the small/large intestine, which were prepared in the previous example, were tested for their functioning in vitro. The granules are mixed in a suitable device, such as a dissolution device, with yoghurt, the pH of which has been measured. Samples are taken for a few hours and the acetaldehyde content is defined. After 4 to 6 hours, the pH of the yoghurt is raised to 7 and the sampling is continued to determine the acetaldehyde content.

The same device can also be used to examine the release of preparations in foodstuffs, which release cysteine in the stomach in a prolonged way.

The invention claimed is:
1. A method for reducing the risk of a cancer of the mouth, the pharynx, the esophagus, the stomach, tile small intestine and the large intestine, comprising administering a non-alcoholic food compositions containing acetaldehyde to humans or for animal feeding, wherein acetaldehyde-binding compound(s) have been added to the food compositions,
wherein the acetaldehyde-binding compound(s) is selected from the group consisting of L-cysteine, D-cysteine, cysteic acid, cysteine glycine, threo- or erythro-β-phenyl-DL-cysteine, β-tetramethylene-DL-cysteine, methionine, L-ascorbic acid, D-penicillamine and its dipeptides with N-terminals, semicarbazide, reduced glutathione, β-mercaptoethylamine, D,L-homocysteine, N-acetylcysteine, L-cysteinyl-L-valine, β-β-tetramethylene-DL-cysteine, cysteinyl-glycine, mercaptoethylglycine, tre-(5)-β-phenyl-DL-cysteine, erythro-β-phenyl-DL-cysteine, cysteine hydrochloride, thiamine hydrochloride, or a salt of any of these compounds, and wherein the amount of acetaldehyde-binding compound in the food compositions is from 0.2 mM to 10 mM/1 μM acetaldehyde.

2. The method according to claim 1, wherein humans take the compositions in connection with consuming alcohol and/or smoking.

3. The method according to claim 1, wherein the acetaldehyde-binding compound contains one or more free sulphhydryl and amino groups.

4. The method according to claim 1, wherein the acetaldehyde-binding compound contains one or more compounds according to the formula (I)

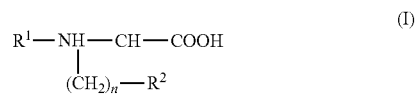

wherein
$R^1$ is hydrogen or an acyl group with 1-4 carbon atoms;
$R^2$ is a sulphhydryl or sulphone group;
n is 1 or 2, or salts of these compounds.

5. The method according to claim 1, wherein the composition comprises an acetaldehyde-binding compound, to which the acetaldehyde binds itself both through a sulphhydryl and an amino group.

6. The method according to claim 1, wherein the composition comprises, L-cysteine, D-cysteine, N-acetylcysteine, or a derivative or salt of cysteine.

* * * * *